(12) United States Patent
Aganyan et al.

(10) Patent No.: US 11,101,044 B2
(45) Date of Patent: Aug. 24, 2021

(54) UBERIZATION AND DECENTRALIZATION OF HEALTHCARE SERVICES

(71) Applicant: Aganyan Inc., Van Nuys, CA (US)

(72) Inventors: Hakop Aganyan, Los Angeles, CA (US); Suren Manukyan, Los Angeles, CA (US); Vagarshak Pilossyan, Los Angeles, CA (US); Leon K. Kiraj, Glendale, CA (US); Inga Aganyan, Sherman Oaks, CA (US); Silvia Aganyan, Los Angeles, CA (US)

(73) Assignee: Aganyan Inc., Van Nuys, CA (US)

( * ) Notice: Subject to any disclaimer, the term of this patent is extended or adjusted under 35 U.S.C. 154(b) by 7 days.

(21) Appl. No.: 16/540,089

(22) Filed: Aug. 14, 2019

(65) Prior Publication Data

US 2019/0385753 A1 Dec. 19, 2019

Related U.S. Application Data

(63) Continuation-in-part of application No. 15/889,691, filed on Feb. 6, 2018, now abandoned.

(51) Int. Cl.
*G16H 80/00* (2018.01)
*G16H 10/60* (2018.01)
(Continued)

(52) U.S. Cl.
CPC .......... *G16H 80/00* (2018.01); *G16H 10/60* (2018.01); *G16H 15/00* (2018.01); *G16H 10/40* (2018.01); *G16H 50/20* (2018.01)

(58) Field of Classification Search
None
See application file for complete search history.

(56) References Cited

U.S. PATENT DOCUMENTS

| 8,983,682 B1 * | 3/2015 | Peeters | B64C 39/024 701/2 |
| 2014/0018779 A1 * | 1/2014 | Worrell | G06F 19/3418 606/1 |

(Continued)

FOREIGN PATENT DOCUMENTS

WO    WO-2017064626 A1 *  4/2017 ........... A61B 5/7465

OTHER PUBLICATIONS

Abo-Zahhad et al, A Wireless Emergency Telemedicine System for Patients Monitoring and Diagnosis, 2014, Int. J. of Telemedicine and Applications, vol. 2014 (Year: 2014).*

*Primary Examiner* — Gregory Lultschik
(74) *Attorney, Agent, or Firm* — Georgiy L. Khayet

(57) ABSTRACT

Methods and systems for providing decentralized healthcare services are provided. An example method may commence with receiving a request for a healthcare service from a patient. The method may continue with providing the request to a responding healthcare provider and receiving a response from the responding healthcare provider. The method may continue with establishing a bidirectional communication between the patient and the responding healthcare provider in real-time and receiving a plan of actions to treat the patient from the responding healthcare provider. The method may further include instructing a diagnostic and laboratory service to physically contact the patient and collect real-time vital parameters of the patient. The method may continue with receiving, from the diagnostic and laboratory service, the real-time vital parameters of the patient and making the real-time vital parameters available to the patient and the responding healthcare provider in an electronic medical record database.

18 Claims, 5 Drawing Sheets

(51) Int. Cl.
*G16H 50/20* (2018.01)
*G16H 10/40* (2018.01)
*G16H 15/00* (2018.01)

(56) References Cited

U.S. PATENT DOCUMENTS

| | | | |
|---|---|---|---|
| 2015/0248536 A1* | 9/2015 | Tawil | G16H 30/20 |
| | | | 705/3 |
| 2015/0370974 A1* | 12/2015 | Zebarjadi | G06Q 10/10 |
| | | | 705/3 |
| 2017/0011193 A1* | 1/2017 | Arshad | G06F 19/3456 |
| 2017/0116384 A1* | 4/2017 | Ghani | H04L 63/08 |
| 2017/0344707 A1* | 11/2017 | Patel | G08G 1/202 |

* cited by examiner

UBERIZATION AND DECENTRALIZATION OF HEALTHCARE SERVICES

CROSS-REFERENCES TO RELATED APPLICATIONS

This application is a continuation-in-part of U.S. patent application Ser. No. 15/889,691, entitled "UBERIZATION AND DECENTRALIZATION OF HEALTHCARE SERVICES," filed on Feb. 6, 2018, which is incorporated herein by reference in its entirety.

BACKGROUND

Technical Field

This disclosure generally relates to computer-implemented methods and systems for providing healthcare services.

Description of Related Art

According to statistical studies, about 3.6 million Americans miss medical appointments each year because of difficulties transportation to a hospital, and the impact of missed primary care appointments is estimated at billions of dollars annually. Millions of people are suffering unnecessarily and thousands are dying because of the bureaucratized procedures of providing healthcare services and heavily legislative system. Restrictions and regulations created in the national healthcare system significantly affected the delivery of available care to patients. In addition, traditional healthcare services are slow and time-consuming as the current healthcare system facilitates multiple doctor visits to obtain a diagnosis. It often takes a few weeks for a patient from a first visit to obtain a diagnosis and a treatment plan. In addition, traditional healthcare services, even in emergency rooms, are delaying immediate doctor-patient contacts, slow in implementation of planned actions, and time consuming. The current system is not doctor and patient friendly, as well as is not designed to be driven by doctor. Even if the doctor makes a decision to act practically, there are designed obstacles and barriers.

Managed care has emerged as the dominant method of health care provision in the United States. Managed care systems assume responsibility for both the financing and provision of health care. Managed care presents new problems for health care practitioners. Managed care systems and all other insurances have been put in the position of gatekeeper, whose responsibilities include cost containment as well as patient care. Some health care commentators have suggested that the new organization of medicine threatens the role of physicians as professionals. Others have called for new models of the physician-patient relationship to accommodate the changes in health care financing.

Most doctors indicate that under managed care physicians are less able to avoid conflicts of interest and less able to place the best interests of patients first. The majority of doctors note that quality of health care is compromised by limitations in location of diagnostic tests and length of and choice of specialists. Most doctors noted a decrease in the physician's ability to carry out ethical obligations, to respect patient autonomy, and to respect confidentiality in physician-patient communication. Many physicians surveyed believe managed care has significant negative effects on the physician-patient relationship, the ability to carry out ethical obligations, and on quality of patient care. These results have implications for health care system and it requires a reform efforts.

Clinicians, medical ethicists, lawyers, and other observers have raised concerns in the areas of the physician-patient relationship, the physician's ethical obligations, and the quality of medical care. Physicians have written personal accounts of their experiences with managed care addressing these same concerns. Professional societies, such as the American Medical Association, have issued guidelines on responding to the challenges managed care poses to the practicing physician.

Studies have addressed the effects of managed care on physician satisfaction, patient satisfaction, and patient outcomes. Survey studies have looked at specific aspects of managed care, such as gatekeeping and capitation, to assess physicians' views. Some state medical societies have surveyed their memberships regarding their general views on managed care. Most of this literature points to new potential conflicts of interest in patient care, as well as challenges for physicians.

The medicine is one of the most humanistic and auspicious field of human activity with rapidly expanding new diagnostic and therapeutic modalities and with highly trained specialists to deliver both the science and art of the medicine. Parallel to this outstanding achievements, when almost instantly, doctors can diagnose and treat life threatening conditions (which were deadly couple of decades ago). Gradually was developed a bureaucratic system which becomes extremely costly, slow to act and in many cases directly impeding evaluation and management of a sick person by creating barriers, obstacles, treatment authorization request processes which by themselves are time consuming, confusing, not goal directed and most importantly are delaying the cure of the patient even when the diagnosis is clear and treatment is available.

The access of the patient to necessary services was restricted and the role and functions of a medical doctor as responsible key decision maker was significantly diminished. The provision of healthcare services is very costly (because of delayed service), fragmented, with multiple obstacles and barriers. Key responsibilities are still on the shoulders of the medical doctor, but decision-making power is shifted to middleman administrative bodies.

This split between the responsibilities and decision-making bodies is destructive to the medicine. This is one of the causes of delay of evaluation and management of problems of the patient along with the "burn out" of the medical doctors. Quality is another issue of the current Health Maintenance Organization (HMO) system, which will not improve unless the middleman is eliminated.

SUMMARY

This section is provided to introduce a selection of concepts in a simplified form that are further described below in the Detailed Description section. This summary is not intended to identify key features or essential features of the claimed subject matter, nor is it intended to be used as an aid in determining the scope of the claimed subject matter.

The disclosure relates to decentralization and uberization of healthcare services. More particularly, the disclosure concerns computer-implemented methods and systems for providing healthcare services. According to one aspect of this disclosure, there is provided a system for providing healthcare services. An example system comprises a healthcare service center including one or more computer servers and at least one database. The healthcare service center can be in communication with user devices of patients and user devices of healthcare providers. For these ends, the system also includes a first user interface configured to provide information to the patients and obtain inputs from the patients using a first graphical user interface displayable on the user devices of the patients. The system also includes a second user interface configured to provide information to the healthcare providers and obtain inputs from the healthcare providers using a second graphical user interface displayable on the user devices of the healthcare providers. The healthcare service center may be configured to receive a request for a healthcare service from a requesting patient. The request for the healthcare service may include at least a selection of a responding healthcare provider. The healthcare service center may provide the request for the healthcare service to the responding healthcare provider. The healthcare service center may further receive, from the responding healthcare provider, a response to the request for the healthcare service. The response may include an acceptance of the request for the healthcare service. Upon the receipt of the response from the responding healthcare provider, the healthcare service center may establish a bidirectional communication between the requesting patient and the responding healthcare provider in real-time. After establishing the bidirectional communication, the healthcare service center may receive, from the responding healthcare provider, a plan of actions to treat the requesting patient. The plan of actions may be available to the requesting patient in an electronic medical record database. The healthcare service center may further receive, from the requesting patient, based on the plan of actions, a selection of a diagnostic and laboratory service. The diagnostic and laboratory service may be associated with a location of the requesting patient and configured to collect real-time vital parameters of the requesting patient. The healthcare service center may instruct the diagnostic and laboratory service to physically contact the requesting patient at the location of the requesting patient and collect the real-time vital parameters. The healthcare service center may further receive, from the diagnostic and laboratory service, the real-time vital parameters of the requesting patient and make the real-time vital parameters available to the requesting patient and the responding healthcare provider in the electronic medical record database. The real-time vital parameters may be used by the responding healthcare provider for selecting a treatment plan for the requesting patient.

According to another aspect of this disclosure, there is provided a method for providing healthcare services. An example method may commence with receiving, from a requesting patient, a request for a healthcare service. The request for healthcare service may include at least a selection of a responding healthcare provider. The method may continue with providing the request for healthcare service to the responding healthcare provider. The method may further include receiving, from the responding healthcare provider, a response to the request for the healthcare service. The response may include an acceptance of the request for the healthcare service. The method may continue with establishing a bidirectional communication between the requesting patient and the responding healthcare provider in real-time. The method may further include receiving, from the responding healthcare provider, a plan of actions to treat the requesting patient. The plan of actions may be available to the requesting patient in an electronic medical record database. The method may continue with receiving, from the requesting patient, based on the plan of actions, a selection of a diagnostic and laboratory service. The diagnostic and laboratory service may be associated with a location of the requesting patient and configured to collect real-time vital parameters of the requesting patient. The method may further include instructing the diagnostic and laboratory service to physically contact the requesting patient at the location of the requesting patient and collect the real-time vital parameters. The method may continue with receiving, from the diagnostic and laboratory service, the real-time vital parameters of the requesting patient and making the real-time vital parameters available to the requesting patient and the responding healthcare provider in the electronic medical record database. The real-time vital parameters may be used by the responding healthcare provider for selecting a treatment plan for the requesting patient.

Additional objects, advantages, novel features, and technical effects of the example embodiments will be set forth in part in the description which follows, and in part will become apparent to those skilled in the art upon examination of the following description and the accompanying drawings or may be learned by production or operation of the example embodiments. The objects and advantages of the concepts may be realized and attained by means of the methodologies, instrumentalities and combinations particularly pointed out in the appended claims. For example, it shall be understood that the technology described in the instant document enables to solve one or more technological problems known in the art, including, for example, the problem of slow, ineffective, and expensive medical data processing and medical data exchange between patients, healthcare service providers, laboratories, pharmacies, and the like.

BRIEF DESCRIPTION OF THE DRAWINGS

Embodiments are illustrated by way of example and not limitation in the figures of the accompanying drawings, in which like references indicate similar elements and in which.

DETAILED DESCRIPTION

Figure 1:
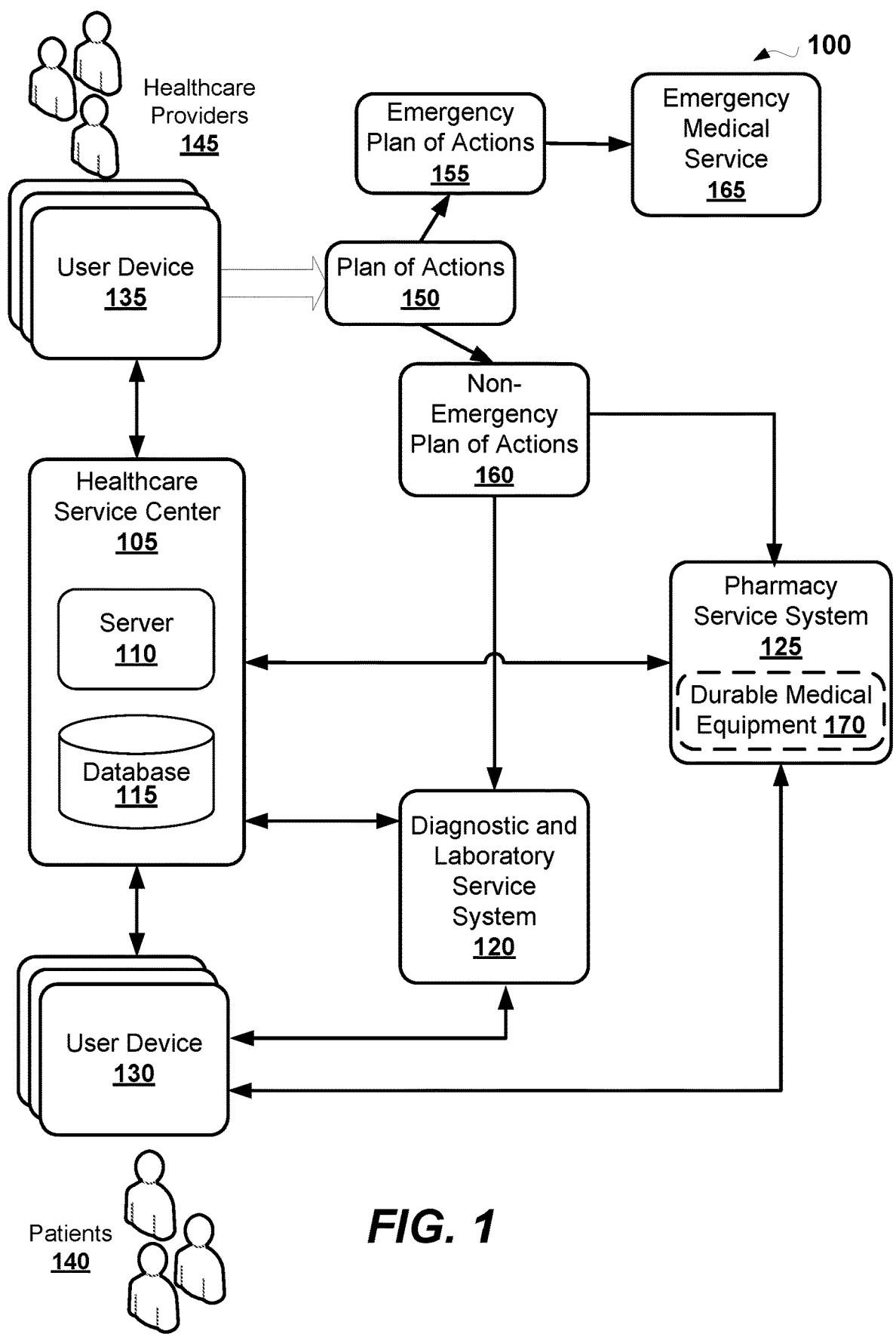
FIG. 1 shows a high-level block diagram of a system architecture suitable for providing healthcare services, according to various example embodiments.

The following detailed description includes references to the accompanying drawings, which form a part of the detailed description. The drawings show illustrations in accordance with exemplary embodiments. These exemplary embodiments, which are also referred to herein as "examples," are described in enough detail to enable those skilled in the art to practice the present subject matter. The embodiments can be combined, other embodiments can be utilized, or structural, logical, and electrical changes can be made without departing from the scope of what is claimed. The following detailed description is, therefore, not to be taken in a limiting sense, and the scope is defined by the appended claims and their equivalents.

For purposes of this patent document, the terms "or" and "and" shall mean "and/or" unless stated otherwise or clearly intended otherwise by the context of their use. The term "a" shall mean "one or more" unless stated otherwise or where the use of "one or more" is clearly inappropriate. The terms "comprise," "comprising," "include," and "including" are interchangeable and not intended to be limiting. For example, the term "including" shall be interpreted to mean "including, but not limited to."

The term "user device" shall mean any electronic device with an input and output modules, and also with electronic communication capabilities. The input modules can include a video camera, keypad, touchscreen, trackball, etc. The output modules can include a display, speakers, etc. Some examples of user devices include, but not limited to, a mobile device, cellular phone, mobile phone, smart phone, Internet phone, netbook, tablet computer, laptop computer, desktop computer, personal digital assistant, workstation, thin client, network node, multimedia player, portable computing device, navigation system, in-vehicle computer, smart television device, set top box, game console, entertainment system, infotainment system, and so forth.

The term "patient" shall mean an individual seeking medical service (e.g., a consultation, examination, etc.) and also a user of a user device. In an example embodiment, the term "patient" shall mean an animal (e.g., a pet of a person) in need of medical service. In this case, the user of the user device may include an owner of the animal and may communicate with a system for providing healthcare services via the user device.

The term "healthcare provider" shall mean a professional who provides healthcare services to patients. Example healthcare providers include a clinician, doctor, physician, specialist (such as a surgeon, radiologist, cardiologist, etc.), dentist, emergency medical technician, physician's assistants, nurse practitioner, nurse, pharmacist, dietician, microbiologist, laboratory expert, laboratory technologist, genetic counselor, researcher, veterinarian, and the like.

Embodiments of the disclosure provide for decentralized systems and methods for providing healthcare services. The systems and methods facilitate uberization of healthcare services, including improvements to collection, storage, distribution, visualization, reporting, and analysis of medical data associated with the healthcare services. As used herein, the term "uberization" means utilization of computing platforms, such as mobile applications, to provide peer-to-peer transactions between clients/patients and health service providers without any middleman central controlling organizations. The transactions may mean sending requests by parties to each other, establishing communication channels, providing services, receiving services, and any other contacts or activities between the parties. An uberized healthcare platform of the present disclosure may also provide recommendations on selecting a healthcare provider based on a distance between the healthcare provider and a patient. In addition, a rating system may be used in the uberized healthcare platforms to rate the quality of the service provided by a healthcare provider and/or rate a patient according to predetermined criteria. The term "uberized" doctor, nurse, diagnostic and laboratory service, or pharmacy service means that a doctor, nurse, diagnostic and laboratory service, or pharmacy service is available as a mobile service. Thus, a doctor, nurse, diagnostic and laboratory service, and pharmacy service can be equipped with a mobile unit to reach a location of a patient and provide healthcare services, perform diagnostic operations, or provide medication to the patient.

According to embodiments of this disclosure, a healthcare service center is provided to connect patients and healthcare providers. The healthcare service center may include one or more computer servers that run a web service accessible by the patients and the healthcare providers via respective user interfaces such as graphical user interfaces available through a website or a software application running on user devices. Both the patients and healthcare providers (e.g., doctors, physicians, dentists, veterinarians, certified healthcare professionals, etc.) can register with the web service and establish patient profiles and healthcare provider profiles, respectively. The healthcare service center may require the healthcare providers to be authenticated and authorized before they can provide medical services via the healthcare service center. The patients can enter their preferences and settings, including, for example, language preferences, residence or location of healthcare providers they are looking for, preexisting medical conditions of the patient, recorded or real-time vital parameters, prior diagnostic data, payment and billing data, patient insurance policy data, contact information, an estimated price or quality of healthcare services that the patient seeks, and so forth. The vital parameters can include but are not limited to blood pressure, pulse, oxygen saturation, blood sugar level, and cholesterol levels. The vital parameters can be measured using various in-home devices/sensors (e.g., wearable devices), self-measured by patients or medical personnel as part of mobile services and transmitted to a platform where they can be accessed by the medical professionals.

The online platform of the present disclosure may enable a direct interaction of a patient, a medical professional (e.g., dentist/hygienist), and a supplemental service provider (e.g., a dental technician), thus eliminating all other existing middlemen (e.g., the Dental Health Maintenance Organization (DHMO) system) who increase the cost of the health care while at the same time decrease the availability of the health care to the patients. Considering the increasing acceleration of the speed of advancement of science and technology in general and particularly in the field of science and art of medicine and especially dentistry, the legality of such interactions can be fully accommodated globally by the use of legal online information technology platforms/services. Today, most of the critical dental equipment that is necessary to perform adequate dental care is available on a mobile scale, the ones needed to perform prophylactic care are in their later generations and the rest are becoming mobile at an ever increasing speed.

It is a well-known fact amongst physicians, that it is significantly cheaper to administer prophylactic care to population compared to treating the disease of the very same people. In other words, being proactive in medicine and especially dentistry costs much less than being reactive. Therefore, the platform of the present disclosure enables the professionals in the field of medicine and especially dentistry be at most proactive on a global level. A dental hygienist equipped with a mobile unit can reach a larger number of families that in case the dental hygienist provides services only at one fixed location, and perform radiographic examination and prophylactic cleaning. Dental x-rays (either partial or full mouth) can be taken by X-ray technicians as part of a mobile service and posted on the platform. Thereafter, medical professionals (e.g., doctors or dentists)

selected to provide services can access the vital parameters. Upon uploading x-ray images of a patient to the platform, the x-ray images can be reviewed by multiple dentists around the world per patients desire, considering religious, cultural, language, linguistic, or other preferences of the patients. Therefore, in view of multiple mutually covering healthcare providers who speak the language of the patient, is knowledgeable of patient culture and/or religion and creates or adds to current health and protection of the patient, there may be no delay of the service to the patient. The preferences and settings of patients can be stored in patient profiles. Each patient may be assigned with a patient identifier, such as a multi-digit access code, which is accessible only to the patient and the healthcare service center. On the other end, the uberized platform may create a competition amongst the healthcare providers for obtaining the right to treat the patient and this competition may be beneficial to the end user, namely to the patient.

In operation, a patient starts using the technology described herein when he wants to seek a medical advice or assistance, for example, when the patient has a medical condition (e.g., a flu, abdominal pain, allergy, etc.) or when he wants to undergo a medical examination (e.g., an annual physical examination).

The patient operates a user device such as a personal computer, smart phone, tablet computer, and the like. The user device of the patient runs a browser or a software (mobile) application that the patient can use to access a website associated with a healthcare service center. The patient sends a request for healthcare services to the healthcare service center via the browser or software application. The request can be for a medical consultation, doctor's opinion, medical prescription, and the like. The request for the healthcare services can be associated with a patient profile or patient preferences as to the language, religion, culture, gender, or location of prospective healthcare providers. Respectively, the patient may be required to create the patient profile before using the healthcare service center.

The request for the healthcare services may include preliminary data about patient's health or medical condition. In one embodiment, the preliminary data may be as simple as what kind of service the patient is seeking. In other embodiments, the preliminary data can include a description of a medical condition, preexisting condition, photographs, videos, or prior medical records. The patient's request is associated with the patient profile. As such, the healthcare service center links the patient's preferences (e.g., a spoken language) to the patient's request.

The healthcare service center selects a healthcare provider based on the request of the patient. The selected healthcare provider is also referred to as a responding healthcare provider. The selection of healthcare provider can vary. In one example, the healthcare service center can process the patient's request and preferences to find the best matching healthcare provider. This process may involve the use of a machine-learning algorithm, heuristic or statistic algorithm. In another example, the healthcare service center can determine what healthcare providers are currently online and available for service, and then send the request of the patient to those healthcare providers. When a group of online healthcare providers receives the request of the patient, the healthcare service center selects the healthcare provider who responded first to the request of the patient. In this scenario, the healthcare service center can also forward the request of the patient to a pre-selected group of healthcare providers based on user preferences. For instance, the healthcare service center can pre-select healthcare providers who speak the language of patient preference or who are from the country (geographical location) of patient preference.

Once the responding healthcare provider is selected, the healthcare service center establishes a bidirectional communication between the patient and responding healthcare provider. For example, a video conference can be established between the user device of the patient and a user device of the responding healthcare provider. The user device of the responding healthcare provider can be a smart phone, laptop computer, tablet computer, desktop computer, and the like. In other implementations, the bidirectional communication includes a voice call, texting, chatting, file sharing, and the like. As such, the healthcare service center provides or facilitates decentralized peer-to-peer transactions or consultations between patients and healthcare providers, bypassing the role of centrally planned corporations and insurance companies.

Upon the communication between the patient and the responding healthcare provider, the responding healthcare provider may request diagnostic services, make prescriptions, request outpatient therapy services, and provide a diagnosis for the patient. The responding healthcare provider can also provide referrals to other healthcare providers or therapy centers to perform additional consultations or procedures. The prescriptions, referrals, diagnoses, and requests by the responding healthcare provider are in a digital form and are associated with the patient profile. Further, the medical prescriptions and requests for therapy procedures may be automatically sent to respective diagnostic and laboratory service systems and pharmacy service systems.

For example, the diagnostic and laboratory service system can perform, manually or automatically, a diagnostic procedure of the patient based on a diagnostic request provided by the responding healthcare provider. Some example diagnostic operations include, but not limited to, collecting and analyzing fluid samples of the patient (e.g., blood work), radiation service (e.g., x-ray, magnetic resonance imaging (MRI), or computed tomography (CT) scans), or imaging service (e.g., ultrasound scan). In some embodiments, the patient does not even need to leave his home for the diagnostic services. Rather, a mobile diagnostic service vehicle can arrive at the location of the patient to perform the diagnostic operation. For example, a vehicle (including a self-driving vehicle) containing diagnostic equipment can arrive at the location of the patient to collect a fluid sample or perform a radiation or imaging scan. The results of diagnostic operations may be electronically transmitted to the responding healthcare provider and also stored in the patient profile. The responding healthcare provider may respond by generating a diagnosis and treatment recommendations for the patient. Those can be also stored in the patient profile and delivered to the patient in a digital form. In some embodiments, the healthcare service system can process available patient data (e.g., the request of the patient, patient profile data, diagnostic operation results, and so forth) to automatically generate a diagnosis or a preliminary diagnosis. For these ends, a machine-learning algorithm can be used.

The patient may be personally responsible for the collection of information from previous episodes of treatment, vaccinations, routine tests and previous hospitalizations and has privileges to add/change records in an electronic medical record (EMR) system. The EMR system may have a plurality of sections, such as past medical history, family and social history, which may be required to be filled out by the patient and/or his family members. Any necessary additions may be done by the healthcare provider.

The responding healthcare provider can also generate a digital prescription for a medication. The digital prescription can be sent automatically to the pharmacy service system. In response thereto, the pharmacy service system can automatically dispatch, ship and deliver the medication to the patient. Similarly, the responding healthcare provider can also generate a request for therapy services for the patient. This request can be electronically delivered to a therapy service provider (e.g., a physical therapy center) to perform the required physical procedures.

Generally, the technology described herein provide for decentralization and uberization of healthcare which is a transition to an economic system where medical doctors, patients, and diagnostic personnel can exchange underutilized capacity of existing assets or human resources, while incurring only low transaction costs. The approaches described in this disclosure has different, much lower operating costs compared to traditional business models.

Importantly, the present technology enables patients to select healthcare providers (e.g., medical doctors) who can be located in any country. As discussed above, the patients can communicate with selected healthcare providers using their preferred language. For example, a Russian-speaking patient located in North America can speak with Russian doctor located in Russia through the technology described herein. An Armenian-speaking patient located in North America can speak with an Armenian-speaking doctor in Armenia using this technology. A Mandarin-speaking patient located in North America can communicate and speak with Mandarin-speaking doctor in China using the technology of this disclosure. There are no limitations as to the languages and countries. If a healthcare provider and a patient speak different languages, interpreters can be used.

After consultation with a healthcare provider, and if a diagnosis is established for a patient, the healthcare provider prescribes the necessary medical treatment, medication or diagnostic services (e.g., a blood work). In this case, the healthcare provider contacts a pharmacy service system through the healthcare service center and the patient receives all necessary medications. If the patient needs a detailed diagnostic examination, the healthcare service center refers to a diagnostic center for 80% less than a market price. The diagnostic center is normally serviced by technical personnel who can work with these diagnostic devices anywhere including from home or mobile services. For example, electrocardiogram (EKG or ECG), ultrasound equipment, MRI, X-ray machine, and other lab equipment can be provided in a vehicle, which can arrive to the patient's location for performing required diagnostic services.

The diagnostic center transfers patient diagnostic results data through the healthcare service center to the appropriate healthcare provider located anywhere in the world for reading the patient diagnostic results data and making an accurate diagnosis. In the process of consulting with a healthcare provider and getting information about health, a patient is highly benefited in an hour, regardless of where the patient is located.

The process of diagnosing and providing information (diagnosis, prescriptions, treatment plans, recommendations, diagnostic results) does not last long, and can be done in a matter of hours. At the request of a patient, the data can be sent to another healthcare provider for a second opinion. In addition, the data of each patient, including patient profiles, are stored in the healthcare service center in an encrypted manner and is accessible only to the patient and the patient's selected healthcare providers through the healthcare service center. Data of each patient may be stored to an electronic health record (EHR) system, or EMR system, which is a systematized collection of patient health information electronically stored in a digital format. A conventionally used EMR standardized in USA and certified by government of USA may be used, in which for each complain and disease process algorithms and guidelines which are attached to the EHR already exist.

Notably, teleconferencing ensures that patients do not infect doctors, medical personnel and other patients. There is no wait time, and the service is much cheaper than traditional medicine routine. Healthcare providers are also available 24 hours a day, seven days a week. It does not matter where a patient is located (at home, work, college, hotel, etc.) to receive qualified medical assistance through the healthcare service center. The patients can receive consultations and individual treatment plans via the healthcare service center. It is also important, there is no need to schedule an appointment. It is also beneficial for people having limited mobility (e.g., disabled or elderly) who can speak with their healthcare providers easily and in real-time. The healthcare providers can be pre-selected for the patients based on language, sex, specialty, affiliation with any hospital, education level and background, rating, ranks, reviews, awards, and the like.

Aspects of the embodiments will now be presented with reference to a system and methods for providing healthcare services. These system and methods are described in this section and illustrated in the accompanying drawings by various blocks, components, steps, operations, processes, algorithms, and the like, collectively referred to as elements. These elements may be implemented using electronic hardware, computer software, or any combination thereof. Whether such elements are implemented as hardware or software depends upon the particular application and design constraints imposed on the overall system.

By way of example, an element, or any portion of an element, or any combination of elements may be implemented with a "processing system" that includes one or more processors. Examples of processors include microprocessors, microcontrollers, Central Processing Units (CPUs), digital signal processors (DSPs), field programmable gate arrays (FPGAs), programmable logic devices (PLDs), state machines, gated logic, discrete hardware circuits, and other suitable hardware configured to perform various functions described throughout this disclosure. One or more processors in the processing system may execute software, firmware, or middleware (collectively referred to as "software"). The term "software" shall be construed broadly to mean instructions, instruction sets, code, code segments, program code, programs, subprograms, software components, applications, software applications, software packages, routines, subroutines, objects, executables, threads of execution, procedures, functions, etc., whether referred to as software, firmware, middleware, microcode, hardware description language, or otherwise. If embodiments of this disclosure are implemented in software, the functions may be stored on or encoded as one or more instructions or code on a non-transitory computer-readable medium. Computer-readable media includes computer storage media. Storage media may be any available media that can be accessed by a computer. By way of example, and not limitation, such computer-readable media can comprise a random-access memory (RAM), a read-only memory (ROM), an electrically erasable programmable ROM (EEPROM), compact disk ROM (CD-ROM) or other optical disk storage, magnetic disk storage, solid state memory, or any other data storage devices, combinations of the aforementioned types of computer-readable media, or any other medium that can be used to store computer executable code in the form of instructions or data structures that can be accessed by a computer.

Referring now to the drawings, exemplary embodiments are described. The drawings are schematic illustrations of idealized example embodiments. Thus, the example embodiments discussed herein should not be construed as limited to the particular illustrations presented herein, rather these example embodiments can include deviations and differ from the illustrations presented herein.

FIG. 1 shows a high-level block diagram of a system architecture 100 suitable for providing healthcare services according to various embodiments of this disclosure. System architecture 100 includes a healthcare service center 105 which includes one or more computer servers 110 and one or more databases 115. It should be noted that the term "server" as used throughout this document refers generally to a computer, a computer program, or a combination thereof. Healthcare service center 105 implements methods for providing healthcare service as described herein by running a software. Healthcare service center 105 can run a web service which can be available to clients (user devices) via Application Programming Interface (API) protocols. In addition, healthcare service center 105 can host a website designed to provide access to the web service and functionality of healthcare service center 105. As such, user devices 130 provide patients 140 with access to a first user interface designed to deliver data to the patients 140 in a visual or audio form, and also obtain data from the patients in the form of text inputs, selections, voice input (which would require natural language processing by healthcare service center 105). Similarly, user devices 135 provide healthcare providers 145 with access to a second user interface designed to deliver data to the healthcare providers 145 in a visual or audio form, and also obtain data from the healthcare providers 145 in the form of text inputs, selections, voice input. Each of the first and second user interfaces could be provided via the website, the software (mobile) application, and the like. Each of the first and second user interfaces could have one or more graphical user interfaces.

System architecture 100 also includes at least one diagnostic and/or laboratory service system 120 and at least one pharmacy service system 125. Diagnostic and laboratory service system 120 refers to an electronic system or facility that performs diagnostic operations to patients. Diagnostic and laboratory service system 120 includes at least one computer or server where patient diagnostic results are collected and stored. Diagnostic and laboratory service system 120 also includes equipment for performing one or more diagnostic or imaging operations such as automated collection and analysis of: patient fluids (e.g., blood, urine, feces, biopsy, etc.), patient images (e.g., x-rays, ultrasound, echo or doppler scans, CT scans, MRI scans, etc.), patient vital parameters (e.g., a height, weight, temperature, heart rate, oxygen value, blood pressure, bone density, etc.), heart operation (e.g., an electrocardiogram, ECG, EKG), and the like. The equipment may include electronic blood pressure monitoring devices, hematology analyzers, chemistry analyzers, X-ray machines, ultrasound devices, and so forth. Diagnostic and laboratory service system 120 can be at a permanent location or fully mobile. For example, diagnostic and laboratory service system 120 can be built-in a vehicle designed to travel to a location of the patient or a preferred location selected by the patient. Once diagnostic and laboratory service system 120 automatically obtains fluids, images, or vital parameters (collectively "diagnostic results data") of the patients 140, diagnostic and laboratory service system 120 transfers them to healthcare service center 105 using secure and encrypted methods. The diagnostic results data is associated with respective patient profiles and stored in database 115. The diagnostic results data can be also become available to respective healthcare providers 145 via user interface. In yet additional embodiments, diagnostic and laboratory service system 120 can include accessories, wearable devices, fitness trackers, portable (wearable) medical monitors, and the like. In this implementation, a wearable device (e.g., a smart watch) can perform collection of certain vital parameters (e.g., temperature, heart rate, blood pressure, etc.) and automatically transfer to healthcare service center 105, where this data is associated with the patient profile and also made available to certain healthcare providers.

Pharmacy service system 125 refers to an electronic system or facility that provides medicine (drugs) to the patients. Pharmacy service system 125 includes at least one computer or server where prescriptions associated with patients are received, stored, and processed. Pharmacy service system 125 also includes equipment for storing and dispatching (shipping) the medication for the patients. As such, pharmacy service system 125 can refer to a brick and motor drug store or a large distribution center where medications are automatically selected, transferred, packaged, and shipped to the patients. The delivery can be performed by mail. In an example embodiment, pharmacy service system 125 may, optionally, provide the delivery of durable medical equipment (DME) 170 to the patients. The DME 170 may include medical equipment used at home by the patients for a higher quality of living. The DME 170 may include blood sugar monitors, blood sugar test strips, canes, catheters, commode chairs, crutches, continuous passive motion devices, wheel chairs, and so forth.

Still referring to FIG. 1, system architecture 100 includes user devices 130 that are operated by patients 140 and user devices 135 that are operated by healthcare providers 145. User devices 130, 135 can be a smart phone or tablet computer enabling the patients 140 and healthcare providers 145 to have bidirectional communication, such as a video or telephone conference. Each user device 130, 135 can include a browser or a software application (e.g., a mobile application) giving access to respective user interfaces.

Healthcare providers 145 may use user devices 135 to develop and provide a plan 150 of actions for patients 140 in the course of a bidirectional communication between healthcare providers 145 and patients 140. Plan 150 of actions may include an emergency plan 155 of actions and a non-emergency plan 160 of actions. If plan 150 of actions developed by one of healthcare providers 145 for one of patients 140 is emergency plan 155 of actions, one of healthcare providers 145 may provide an instruction to healthcare service center 105 to forward an emergency medical service 165 to one of patients 140. Emergency medical service 165 may include an uberized ambulance forwarded to a location of one of patients 140. If plan 150 of actions developed by one of healthcare providers 145 for one of patients 140 is non-emergency plan 160 of actions, one of healthcare providers 145 may provide a digital diagnostic request to collect real-time vital parameters of one of patients 140 using diagnostic and laboratory service system 120. The diagnostic and laboratory service system 120 may include an uberized laboratory service, which may be forwarded to the location of one of patients 140 based on the instruction of one of healthcare providers 145. Furthermore, if plan 150 of actions is non-emergency plan 160 of actions, one of healthcare providers 145 may provide a prescription for one of patients 140 and provide an instruction to healthcare service center 105 to dispatch (ship) the medication to one of patients 140 in accordance with the prescription using pharmacy service system 125. The pharmacy service system 125 may include an uberized pharmacy service, which may be forwarded to the location of one of patients 140 based on the instruction of one of healthcare providers 145.

Accordingly, system architecture 100 provide for decentralized and automated collection, distribution, and analysis of medical information through user devices. Embodiments facilitate the entry, storage, tracking, visualization, and analysis of comprehensive personal health information.

In additional embodiments, system architecture 100 further includes a payment processing system configured to process online payments of the patients 140. Healthcare service center 105 can be in operative communication with the payment processing system in order to being able to cause the payment processing system to process a payment of the patients for healthcare services.

In yet other embodiments, healthcare service center 105 can be in communication with an insurance claim system. Healthcare service center 105 is further configured to cause the insurance claim system to provide a payment to the requesting patient or the responding healthcare provider for healthcare services provided by the healthcare provider.

Figure 2:
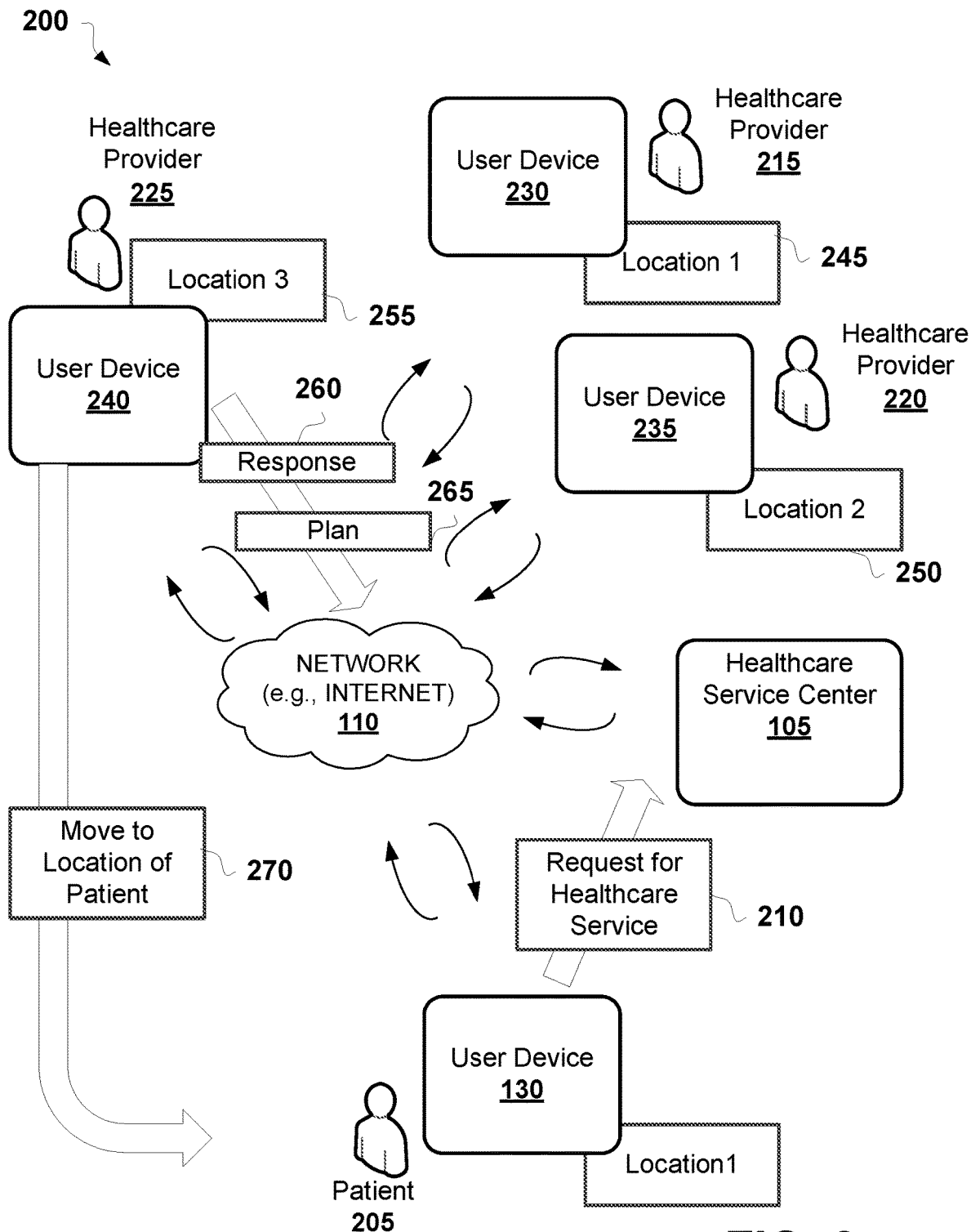
FIG. 2 is a schematic diagram illustrating a system for providing healthcare services, according to an example embodiment.

FIG. 2 is a schematic diagram illustrating a system 200 for providing healthcare services, according to an example embodiment. The system 200 may include a healthcare service center 105. The healthcare service center 105 may include one or more computer servers and at least one database and may be in communication with user devices of a plurality of patients and user devices of a plurality of healthcare providers. The system 200 may further include a first user interface configured to provide information to the plurality of patients and obtain inputs from the plurality of patients using a first graphical user interface. The first graphical user interface may be displayable on the user devices of the plurality of patients. The system 200 may further include a second user interface configured to provide information to the plurality of healthcare providers and obtain inputs from the plurality of healthcare providers using a second graphical user interface. The second graphical user interface may be displayable on the user devices of the plurality of healthcare providers.

Healthcare service center 105 may be connected to diagnostic and laboratory service system 120, pharmacy service system 125, one or more user devices 130, and one or more user devices 135 (as shown on FIG. 1) via at least one communications network. The communications network refers to any wired, wireless, or optical networks including, for example, the Internet, intranet, local area network (LAN), Personal Area Network (PAN), Wide Area Network (WAN), Virtual Private Network (VPN), cellular phone networks (e.g., Global System for Mobile (GSM) communications network, packet switching communications network, circuit switching communications network), Bluetooth radio, Ethernet network, an IEEE 802.11-based radio frequency network, a Frame Relay network, Internet Protocol (IP) communications network, or any other data communication network utilizing physical layers, link layer capability, or network layer to carry data packets, or any combinations of the above-listed data networks.

The healthcare service center 105 may be configured to receive, from a requesting patient shown as a patient 205, patient data. The patient data may include at least medical data and a location of the requesting patient 205. The healthcare service center 105 may store the patient data to an EMR database. The healthcare service center 105 may further prompt the requesting patient 205 to enter the medical data. The medical data may be associated with one or more of the following: a current health condition, previous treatment episodes, vaccinations, routine tests, hospitalizations, and so forth.

The healthcare service center 105 may further receive, from the patient 205, a request 210 for a healthcare service. The request 210 for healthcare service may include at least a selection of a responding healthcare provider. Specifically, the patient 205 review a list of all available healthcare providers, such as a healthcare provider 215, a healthcare provider 220, and a healthcare provider 225. The healthcare provider 215 may communicate with the healthcare service center 105 using a user device 230, the healthcare provider 220 may communicate with the healthcare service center 105 using a user device 235, and healthcare provider 225 may communicate with the healthcare service center 105 using a user device 240. Healthcare providers may be located at different locations, e.g., the healthcare provider 220 may be located at location 1 245, the healthcare provider 225 may be located at location 2 250, and the healthcare provider 230 may be located at location 3 250. The patient 205 may select the healthcare provider 225 in the request 210. The healthcare service center 105 may be configured to provide the request 210 for the healthcare service to the responding healthcare provider, i.e. the healthcare provider 225.

The healthcare service center 105 may receive, from the responding healthcare provider 225, a response 260 to the request for the healthcare service. The response 260 may include an acceptance of the request 210 for the healthcare service. Upon the receipt of the response 260 from the responding healthcare provider 225, the healthcare service center 105 may establish a bidirectional communication between the requesting patient 205 and the responding healthcare provider 225 in real-time. Therefore, direct communications between the patient 205 and the healthcare provider 225 may be established immediately upon the request of the patient, provided that the patient 205 can choose the healthcare provider 225 and the healthcare provider 225 can choose whether to accept the request of the patient 205.

After establishing the bidirectional communication, the healthcare service center 105 may receive, from the responding healthcare provider 225, a plan 265 of actions to treat the requesting patient 205. The plan 265 of actions may be made available to the requesting patient 205 in an EMR database. In an example embodiment, the receipt of the plan 265 of actions may include receiving of one of an emergency plan of actions and a non-emergency plan of actions. The receipt of the emergency plan of actions may include receiving an instruction to forward an emergency medical service to the requesting patient 205 or move, by the healthcare provider 225, personally to the location of the patient 205, as shown by block 270. The receipt of the non-emergency plan of actions may include receiving a digital diagnostic request to collect the real-time vital parameters of the requesting patient 205.

The healthcare service center 105 may receive, from the requesting patient 205, based on the plan 265 of actions, a selection of a diagnostic and laboratory service. The diagnostic and laboratory service may be associated with a location of the requesting patient 205 and configured to collect real-time vital parameters of the requesting patient 205. The healthcare service center 105 may instruct the diagnostic and laboratory service to physically contact the requesting patient 205 at the location of the requesting patient 205 and collect the real-time vital parameters. In an example embodiment, the diagnostic and laboratory service may be a mobile service configured to move to the location of the requesting patient 205 upon the receipt of the instruction to physically contact the requesting patient 205.

The healthcare service center 105 may receive, from the diagnostic and laboratory service, the real-time vital parameters of the requesting patient 205 and make the real-time vital parameters available to the requesting patient 205 and the responding healthcare provider 225 in the EMR database. The real-time vital parameters may be used by the responding healthcare provider 225 for selecting a treatment plan for the requesting patient 205.

In an example embodiment, based on the location of the requesting patient 205 and the plan of actions received from the responding healthcare provider 225, the healthcare service center 105 may instruct the responding healthcare provider 225 to move to the location of the requesting patient 205 to provide treatment according to the plan 265 of actions.

Upon terminating the bidirectional communication, the healthcare service center 105 may receive a further request from the requesting patient 205 to contact the responding healthcare provider 225. In response to the request, the healthcare service center 105 may re-establish the bidirectional communication between the requesting patient 205 and the responding healthcare provider 225.

Upon terminating the bidirectional communication, the healthcare service center 105 may receive a further request from the responding healthcare provider 225 to contact the requesting patient 205. In response to the request, the healthcare service center 105 may re-establish the bidirectional communication between the responding healthcare provider 225 and the requesting patient 205. Therefore, after the first contact, the patient 205 and the doctor 225 can directly communicate with each other to ask additional questions or monitor the treatment progress.

In the need to follow the patient, the progress of disease, the effect of medications and the process of patient education, uberization and decentralization of healthcare services creates an opportunity to contact with the healthcare provider if the patient has a question and to call the patient if the healthcare provider has additional question. This condition of continuing immediate and direct doctor-patient contact with cultural, religious/faith, language communication is always expected but not existing in conventional healthcare systems. This may eliminate confusion which can occur when the condition of the patient deteriorates or other unexpected turns of health condition of the patient occur. The uberized healthcare provider may follow the patient until the end of the treatment, if the patient wishes, and it is the responsibility of the healthcare provider to involve specialists, diagnostics and paramedical services into treatment process as deemed necessary during the re-evaluation and management of the patient. The healthcare provider is directly responsible for evaluation and treatment of the patient condition without waiting for approval from administrative authorities.

The healthcare service center 105 may receive a digital prescription from the responding healthcare provider 225. The digital prescription may be associated with the requesting patient 205. The healthcare service center 105 may select and cause one of a plurality pharmacy service systems to deliver a medication to the requesting patient 205 in accordance with the digital prescription. The one of a plurality pharmacy service systems may be associated with the location of the requesting patient 205.

In an example embodiment, the healthcare service center 105 may make the real-time vital parameters of the requesting patient 205 available to a plurality of healthcare providers via the EMR database. The healthcare service center 105 may receive, from one or more of the plurality of healthcare providers, one or more requests to provide healthcare services to the requesting patient. The healthcare service center 105 may report to the requesting patient 205 the one or more requests from the one or more of the plurality of healthcare providers and receive, from the requesting patient 205, a selection of one of the one or more of the plurality of healthcare providers. Based on the selection, the healthcare service center 105 may establish a further bi-directional communication between the requesting patient 205 and the one of the one or more of the plurality of healthcare providers.

Healthcare providers, such as the Medicine Doctors and Doctors of Osteopathy, may become the key drivers of the healthcare system from the beginning until the end of evaluation and management process. In particular, the innovation of the model is that the healthcare providers are initiating and carrying the task forward according their impression. No other specialist is trained and ready enough to start and follow the evaluation and management. All middleman, secretary, appointment giving, authorization requesters, follow up steps are done immediately, directly without delay and involvement of middlemen and using the system of the present disclosure.

Since the beginning of interaction of the patient, the healthcare provider determines where the case of the patient is an acute, sub-acute or chronic case. Chest pain, sever shortness of breath, altered mental status need a call of involvement of emergency medical services, paramedics and transfer to the emergency room with recommendations for the most probable cause predicted. In sub-acute cases, the doctor healthcare provider may activate home emergency services for EKG, blood and urine collection, and so forth.

In chronic cases, the healthcare provider is following an evidence-based guidelines and recommendation. No case and no procedure and analysis of results are done by any other person except the healthcare provider. This provides sacredness of doctor-patient relationship with modern information technology when the bedside clinical diagnosis is done at distance by using modern information technology.

The patient with chronic conditions may need to inform the healthcare provider daily or even hourly about vital signs of the patient and the results of appropriate measurements. Due to of the epidemic of the hypertension, daily measurements of the blood pressure on both arms, even if there is a need of 3-4 or more measurements, may be done by the patient (or by an uberized nurse). In an example embodiment, every patient that uses the system of the present disclosure may be educated on how to take vital signs of the patient, such as ECG with basic heart rate and rhythm assessment, carbon dioxide level (partial pressure of carbon dioxide, $_pCO_2$) by finger sensor with respiratory rate and FEV1/FVC ratio (Tiffeneau-Pinelli index) measurement, blood sugar, urine dipstick tests, and so forth. This simplified basic initial work up can save time needed for the of the emergency medical service visit or hospitalization or speed up the delivery of emergency medical service to the patient. Therefore, uberization of the emergency medical service and doctor-patient interaction may simplify human to human (doctor-patient) relationships to the basic level, when the patient may be more engaged in his/her health and self-monitoring under the direct supervision and guidance of the healthcare provider.

The assessment by the healthcare provider of the volume status (jugular vein distention, edema of legs, heart rhythm and rate) of the patient followed by appropriate medical intervention in site may trigger a nursing visit or dispatch of an emergency medical service to a location of the patient. This immediate-direct-feedback interaction between the patient and the healthcare provider may not just increase the chance of controlling the blood pressure by decreasing it, but it also directly teaches the patient how the healthcare provider makes decisions and acts in similar conditions, which is an invaluable educational tool and is easy to use during future disease episodes. The "uberized visit action", e.g., a visit of the uberized nurse to the patient, is not over if the problem is not solved and follow up is not done. The same model is correct for a diabetic patient who needs hourly blood sugar measurement and immediate medical intervention by insulin or oral medication with follow up 24 hour a day. In critical cases of the disease/condition, the healthcare provider may organize a visit of the emergency medical service to the location of the patient and continue follow-up. Patients with asthma, chronic kidney disease, congestive heart failure, arrhythmia, anemia, urticaria, osteoarthritis, etc. may have the same access to communications with the healthcare provider without mediators and with immediate actions to follow.

Data associated with patients, who for some reason are refusing, rejecting or not following advises of healthcare providers, may be also stored into systems of the present disclosure. During multiple interactions with the healthcare provider, a patient may be receiving more information about condition of the patient and create sufficient data for making true informed decisions by the healthcare providers in association with this patient other further patients. Conventional healthcare systems are not designed for true informed consent and informed decision making by the healthcare provider. Starting from the first contact until the end of life decisions, the style of doctor-patient relationship may change dramatically if the doctor is sensitive to cultural, religious, moral issues of the patient by keeping the care-comfort and treatment goals as a priority. Understanding between healthcare providers and patients is a process which includes also behavioral, attitudinal and habit changes as a necessary ingredients of self-realization and there must be minimum necessary critical information about a disease process of a sick person. This constant, open "uberized and decentralized communication dialogs" between healthcare providers and patients cannot be provided by conventional healthcare systems.

Uberization of providing healthcare services may eliminate nonsensical but legalized requirements which are-time consuming and anti-medicine acts created by insurance companies and authorities. The classical example of adverse effect of legalized requirements on provision of healthcare services relates to prescription for medication Entresto (sacubitril/valsartan), which has class one recommendation. In particular, it was considered unethical to continue double blind controlled study, and it was prematurely stopped, because many people were dying in a controlled arm of the study. Yet if a doctor decided to prescribe this medication, the doctor is obliged to copy the guidelines, prove the class one recommendation, fill a treatment authorization request (TAR) form, prove that other treatments failed, and wait approval of officers who never saw or examined the patient. There is a possibility that the patient can die during a waiting period. The response like "not enough evidence" demands the doctor to fill another TAR form. Studies had shown that 20-25% of cases the second TAR is not filled. The methods and systems of the present disclosure are designed to save money and cut expenses of patients and medical and governmental institutions. The death will be justified by the severity of the disease process, not by the delay of service to be provided to the patient. The uberization of providing healthcare services may eliminate these and similar misfortunes and save lives.

Healthcare in general is a highly regulatory environment. Conventionally, the most complex issue is complex interactions between insurers, consumers, and health care providers. By uberization and decentralization of providing the healthcare services, the methods and system of the present disclosure intend to disrupt current heavily bureaucratic system by re-establishing the central role of a doctor and sacredness of doctor-patient relationship in the health care system and by using a technology to circumvent unnecessary bureaucracy and legislation. Uberization and decentralization of medicine with the medical doctor in a center with doctor-patient relationship as the most sacred unit may eliminate all the barriers and obstacles created in the conventional healthcare system and eliminate infringing doctor's free will and patient's rights in view of sending the patient back to the doctor for the same problem when the doctor is asking for necessity of another action.

The methods and systems of the present disclosure intend to require much lower costs compared to a traditional Managed Care business or HMO. In particular, the methods and systems do not require buying vehicles or any medical equipment and establishing medical centers, but allow individuals in all segments of medical field to work for themselves all over the world without borders with their own language, preferred faith, or religion and in any field of medicine, including traditional, folk, holistic, and alternative medicine.

Uberization and decentralization of healthcare services may eliminate the concept of non-covered services by insurance companies and eliminate the currently used concept by health insurance companies that "the doctor is not in our network". With a model used in the system of the present disclosure, every doctor has a free choice to choose a patient and any patient has a free choice to choose the doctor.

Additionally, a mobile healthcare service (e.g., Dental Hygiene service) may treat a patient at a patient request at any given location. Any healthcare professional or patient may operate or use a messaging or communication platform with a database which can be integrated with the existing infrastructure of GSM operators and Voice over Internet Protocol (VoIP) companies and take advantage of all their capabilities.

A streaming technology may be used to ensure low data usage, smart internet channel for data transmission, and fast and smart recovery for lost packages. The Over the Top (OTT) messaging which is highly scalable and 5× lightweight may be used. To provide high level integrability, the following communication channels may be used: eXtensible Messaging and Presence Protocol (XMPP), Session Initiation Protocol (SIP), Short Message Peer-to-Peer (SMPP), and Hypertext Transfer Protocol (Secure) (HTTP(S)).

Figure 3:
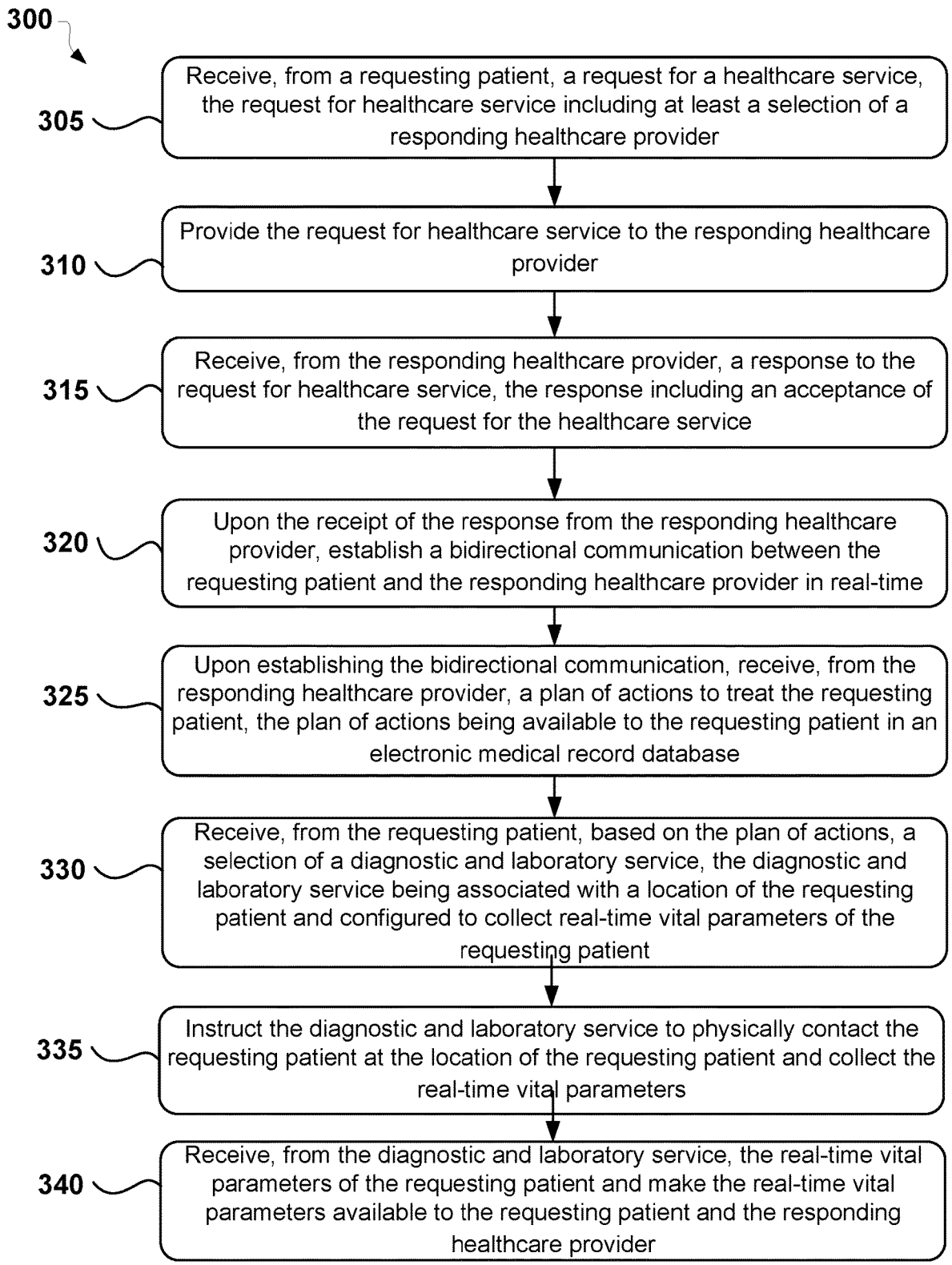
FIG. 3 is a process flow diagram showing a method for providing healthcare services, according to an example embodiment.

FIG. 3 is a process flow diagram showing a method 300 for providing healthcare services according to an example embodiment. Method 300 may be performed by processing logic that may comprise hardware (e.g., decision-making logic, dedicated logic, programmable logic, application-specific integrated circuit (ASIC), and microcode), software (such as software run on a general-purpose computer system or a dedicated machine), or a combination of both. In one example embodiment, the processing logic refers to healthcare service center 105 or any of its components. Below recited operations of method 300 may be implemented in an order different than described and shown in the figure. Moreover, method 300 may have additional operations not shown herein, but which can be evident for those skilled in the art from the present disclosure. Method 300 may also have fewer operations than outlined below and shown in FIG. 3.

Method 300 commences with maintaining a healthcare service center that includes one or more computer servers and at least one database as shown in FIG. 1. As discussed above, the healthcare service center is configured to provide a web service for one or more patients and one or more healthcare providers. The web service provides a first user interface for serving information to the patients and obtaining inputs from the patients through one or more graphical user interfaces displayable on user devices. Similarly, the web service provides a second user interface for serving information to the healthcare providers and obtaining inputs from the healthcare providers using one or more graphical user interfaces displayable on user devices of the healthcare providers. The first and second user interfaces are configured to receive inputs in the form of text, images, selections, touches, taps, voice, video, audio, tactile, haptic, and other inputs, and also configured to deliver outputs in the form of the form of text, images, video, audio, tactile, haptic, and other inputs.

The web service enables the patients to remotely create or modify patient profiles, which can be stored in the database. The patient profiles can include, for example, a patient name, address and contact information, payment data (e.g., credit card information), healthcare insurance data, credentials (e.g., a login and password), photographs, images, videos, data concerning medical history, data concerning pre-existing conditions, data concerning health issues, diagnostic reports, medical needs, and the like. The patient profiles can also include one or more patient preferences, including, for example, a patient spoken language, a preferred language of healthcare provider, a preferred location of healthcare provider, a preferred hospital affiliation of healthcare provider, a preferred specialty of healthcare provider, and the like.

Similarly, the web service enables the healthcare providers to remotely create or modify healthcare provider profiles, which can be stored in the database. The healthcare provider profiles can include, for example, a name of healthcare provider, address (location) and contact information, specialty (e.g., a family medicine practitioner, cardiologist, ear, nose, and throat (ENT), urologist, dermatologist, neurologist, etc.), medical license data, education information, hospital affiliation data, spoken languages, preferred rates, preferred times or schedule of service, banking information, and other necessary personal information.

Before a certain healthcare provider can provide services through the healthcare service center, the healthcare provider must be authenticated and authorized. As such, in method 300, the healthcare service center authenticates and authorizes the healthcare provider to remotely provide healthcare services to the patients using the healthcare service center. The authentication can involve verifying healthcare provider identity (e.g., through a login and password, two-step verification methods, etc.). The authorization is required to verify that the healthcare provider is duly licensed to provide professional services by a local government. The authorization may involve obtaining medical license data or education information and automatically verifying that the healthcare provider is in a good standing and duly authorized to provide medical services based on the medical license data or education information.

Referring now back to FIG. 3, method 300 continues at block 305 with the healthcare service center obtaining a request for a healthcare service from a requesting patient. The request can be input by the patient by a text or voice. If it is a voice input, the healthcare service center applies a natural-language processor to transform the voice input into a text input. The input of the patient can include one or more healthcare needs or preferences. For example, the request can specify one or more of the following: patient medical need (e.g., to seek a consultation, to perform a check-up, etc.), a medical condition or concern (e.g., abdominal pain, rash, high temperature, etc.), healthcare provider specialty (e.g., a family doctor, neurologist, gastroenterologist, etc.), preferred language (e.g., English, German, Spanish, French, Russian, etc.), preferred location of healthcare provider (e.g., the United States, Germany, France, Europe, Russia, South Korea, Japan, etc.), and one or more patient's images, videos, audio, and medical data. The request for healthcare service may also include a selection of a responding healthcare provider from a list of available healthcare providers.

At block 310, the healthcare service center provides the request for healthcare service to the responding healthcare provider. At block 315, the healthcare service center receives, from the responding healthcare provider, a response to the request for the healthcare service. The response may include an acceptance of the request for the healthcare service.

At block 320, upon the receiving the response from the responding healthcare provider, the healthcare service center selectively establishes a bidirectional communication between the requesting patient and a responding healthcare provider in real-time and in accordance with the request for the healthcare service obtained from the requesting patient at block 205.

The healthcare service center can automatically select a list of healthcare providers for the patient from a plurality of healthcare providers by matching the patient preferences or data obtained from the request to the data and preferences of healthcare providers. The matching can be based on scoring and sorting of patient related and healthcare provider related information. In some embodiments, a machine-learning system can be used to perform the matching. In other embodiments, the healthcare service center can preselect a certain group of healthcare providers but then enables the preselected healthcare providers to respond in real time to the request of the patient. The bidirectional communication between the requesting patient and the responding healthcare provider can include one or more real-time data exchange methods such as a video conference, voice call, text chat, file sharing, and the like.

In an example embodiment, the pre-selection of a responding healthcare provider by the healthcare service center may be performed as follows. The healthcare service center may automatically generate a proposal to provide a healthcare service for the requesting patient. The proposal can be generated based on the request for the healthcare service obtained from the requesting patient at block 305. The healthcare service center may pre-select one or more of the healthcare providers based on parameters of the request for the healthcare service obtained from the requesting patient or based on preferences of the requesting patient stored in the patient profile. The parameters of the request include at least one of requesting patient preferences, such as a preferred language of the responding healthcare professional and a residence of the responding healthcare professional. In some embodiments, the healthcare service center can pre-select all of the healthcare providers authorized with the web service. In other embodiments, the healthcare service center may pre-select only those healthcare providers who are currently online. The healthcare service center may distribute the proposal to the pre-selected healthcare providers. When received, the proposal can be displayed using the second user interface on a screen of user device of the pre-selected healthcare providers. The healthcare service center may receive a response to the proposal from responding healthcare providers using the second user interface. The healthcare service centers may provide a list of responding healthcare providers, which agreed to provide the healthcare service, to the requesting patient.

At block 325, upon the establishing the bidirectional communication, the healthcare service center receives, from the responding healthcare provider, a plan of actions to treat the requesting patient. The plan of actions may be made available to the requesting patient in an EMR database. At block 330, the healthcare service center may receive, from the requesting patient, based on the plan of actions, a selection of a diagnostic and laboratory service. The diagnostic and laboratory service may be associated with a location of the requesting patient and configured to collect real-time vital parameters of the requesting patient. The healthcare service center may recommend a plurality of diagnostic and laboratory services located at or close to the location of the requesting patient. The requesting patient may select the diagnostic and laboratory service from the provided list.

At block 335, the healthcare service center may instruct the diagnostic and laboratory service to physically contact the requesting patient at the location of the requesting patient and collect the real-time vital parameters. Some example laboratory operations performed by the diagnostic and laboratory service can include collecting and analyzing any body fluids or materials of the requesting patient (e.g., blood, urine, saliva, feces, biopsy sample, etc.). Some example diagnostic operations can include collecting vital parameters (e.g., a heart rate, blood pressure, oxygen level in a blood stream, bone density, body temperature, height, weight) or performing imaging or radiology services (e.g., ultrasound, ECG, MRI, CT, X-ray scans, etc.). Any or all of the laboratory and diagnostic operation can be fully automated.

At block 340, the healthcare service center may receive, from the diagnostic and laboratory service, the real-time vital parameters of the requesting patient and make the real-time vital parameters available to the requesting patient and the responding healthcare provider in the EMR database. The real-time vital parameters may be used by the responding healthcare provider for selecting a treatment plan for the requesting patient.

In an example embodiment, the healthcare service center may automatically produce or receive from the responding healthcare provider a diagnosis of the requesting patient, medical recommendations for the requesting patient, and at least one of a digital diagnostic request, a digital therapy request, and a digital prescription. Any or all of this information can be delivered to the requesting patient through the healthcare service center and also stored in the patient profile of the requesting patient. For example, the diagnosis and the diagnostic requests can be entered by the responding healthcare provider via a corresponding user interface. In another example, healthcare service center 105 can automatically recommend and deliver a preliminary diagnosis, any required diagnosis or therapy requests, and prescriptions based on data obtained from the requesting patient or the responding healthcare provider.

In some embodiments, the healthcare service center may automatically create one or more recommendations to the requesting patient based on the diagnosis or the digital diagnostic request. The healthcare service center can also transmit the recommendations to the requesting patient.

Optionally, the healthcare service center may select and cause one of pharmacy service systems to provide medication to the requesting patient in accordance with the digital prescription (if any). Particularly, the healthcare service center can select and cause one of pharmacy service systems to receive the digital prescription from the responding healthcare provider and deliver a medication to the requesting patient in accordance with the digital prescription. The selected pharmacy service system may be located close to the location of the patient to facilitate quick delivery of the medication. The delivery operation can include shipping and forwarding the medication personally by an operator of the pharmacy service systems or by mail.

Similarly, the healthcare service center can further receive a digital referral from the responding healthcare provider. The digital referral may be associated with the requesting patient. In response to the referral, the healthcare service center may select and cause one of physical therapy systems to provide a physical therapy service to the requesting patient in accordance with the digital referral. The physical therapy systems can include automated or manual physical therapy equipment, including, for example, cardiovascular and pulmonary physiotherapy, clinical electrophysiology, geriatric therapy, integumentary therapy, neurological therapy, orthopedic therapy, sports therapy, physiotherapy therapy, and the like.

In addition, the healthcare service center may update the patient profile of the requesting patient with the diagnosis, any requests for therapy or diagnosis, medical prescriptions (if any), a summary of medical consultation, one or more health recommendations, and the like.

Additionally, when the requesting patient undergoes a diagnostic procedure as requested by the responding healthcare provider, diagnostic and laboratory service system may automatically generate diagnostic reports reflecting collected and analyzed medical data of the requesting patient. Further, diagnostic and laboratory service system may transmit the diagnostic report to healthcare service center, and healthcare service center may store the diagnostic report in database such that the diagnostic report is associated with the requesting patient in database. Further, healthcare service center can automatically determine a preliminary diagnosis of the requesting patient based at least in part on the diagnostic report. Healthcare service center may also provide a suggestion message containing the preliminary diagnosis to the requesting patient or the responding healthcare provider. The preliminary diagnosis can also be stored at least temporary in the patient profile. The preliminary diagnosis can be created by using a machine-learning algorithm.

Similarly, the requesting patient can have one or more medical equipment suitable to collect vital parameters. For example, the requesting patient can have fitness trackers, electronic blood pressure monitors, wireless scales, medical trackers, and the like, which can automatically collect and transmit the vital parameters to the healthcare service center in real time. The healthcare service center may store the real-time vital parameters in the database such that they are associated with the requesting patient. Further, the healthcare service center may automatically determine a preliminary diagnosis of the requesting patient based at least in part on the real-time vital parameters and provide a suggestion message containing the preliminary diagnosis to the requesting patient or the responding healthcare provider.

Figure 4:
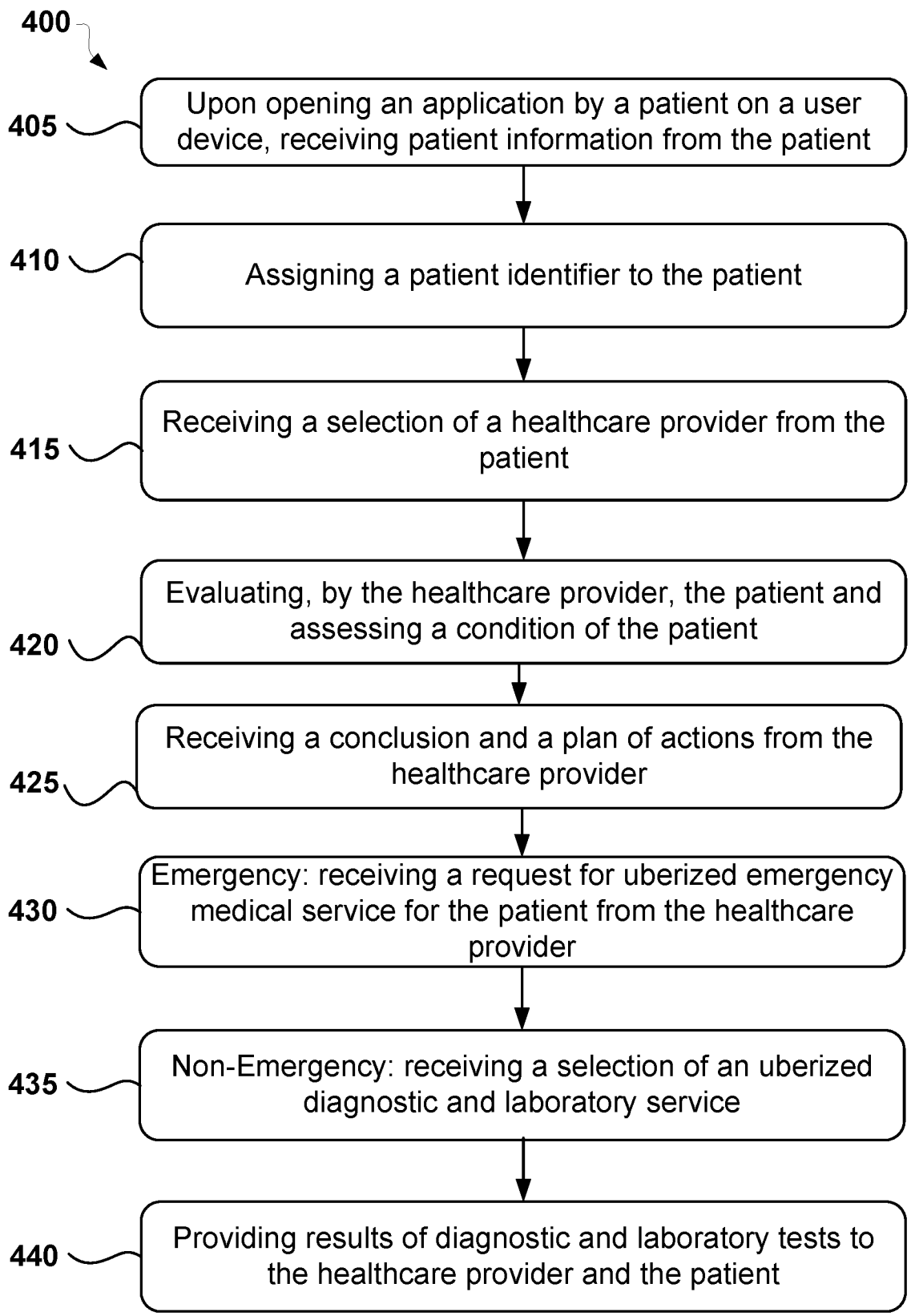
FIG. 4 is a flow diagram illustrating steps performed by a patient, a healthcare provider, and a healthcare service center in the course of providing a healthcare service to the patient by the healthcare provider, according to an example embodiment.

FIG. 4 is a flow diagram illustrating operations performed by a patient, a healthcare provider, and a healthcare service center in the course of providing a healthcare service to the patient by the healthcare provider, according to an example embodiment. The providing of a healthcare service includes providing a real-time medical service to the patient to achieve an intended goal of uberization and decentralization of healthcare services with advanced and fast assessment of condition of the patient and provision of a conclusion with the plan of action by the healthcare provider.

At block 405, the patient may open an application running on a user device, optionally select a language, and enter/provide patient information. At block 410, the healthcare service center may assign a patient identifier to the patient for security purposes.

At block 415, the healthcare service center may receive a selection of the healthcare provider made the patient. For example, the patient may select the healthcare provider based on a location of the healthcare provider, e.g., the healthcare provider that is closest to the location of the user.

At block 420, the healthcare provider may evaluate the patient and assess a condition or a disease of the patient. At block 425, the healthcare provider may receive a conclusion on a condition of the patient and a plan of actions from the healthcare provider. At block 430, in case the plan of actions is an emergency plan of actions, the healthcare service center may receive a request for an emergency medical service, namely an uberized paramedics or ambulance, for the patient from the healthcare provider. At block 435, in case the plan of actions is a non-emergency plan of actions, the healthcare provider may provide an instruction to forward the uberized diagnostic and laboratory service to the patient. The healthcare service center may receive a selection of an uberized diagnostic and laboratory service (e.g., a dental hygiene service, a dentist, an uberized nurse, a blood laboratory) from the patient (e.g., the uberized diagnostic and laboratory service closest to the location of the patient). The uberized mobile diagnostic and laboratory service may include a mobile unit configured to move to the location of the user. In an example embodiment, the uberized diagnostic and laboratory service may include a self-driving car configured to drive to the location of the user and provide pickup and delivery of medical services, such as pharmacy delivery, urine pickup, or pickup of any physiological materials (e.g., saliva, blood, hair) of the user and deliveries of any other services/products. The delivery of medical services may include delivery of DME. The DME may include any equipment that provides therapeutic benefits to a patient in need because of certain medical conditions and/or illnesses of the patient. The DME includes items which are primarily and customarily used to serve a medical purpose. At block 440, the healthcare provider may provide results of diagnostics and laboratory tests to the healthcare provider and the patient. Additionally, if the plan of actions is a non-emergency plan of actions, the healthcare provider may provide an instruction to dispatch (ship) the medication to the patients using a pharmacy service system. The pharmacy service system may include an uberized pharmacy service, which may be forwarded to the location of the patient based on the instruction of the healthcare provider. In an example embodiment, the uberized pharmacy service may include a self-driving car configured to drive to the location of the user.

Uberized doctor-patient interaction may be not considered completed by the system until the action is not materialized, i.e. until the service is provided to the patient. In case the condition of the patient is life threatening (for example, a person is having a heart attack or severe allergic reaction), the patient himself or an uberized medical doctor can call or would recommend to call, through the communication platform of the system of the present disclosure, uberized paramedics/ambulance. Once the patient location have been matched the closest paramedic or ambulance, the system may send the closest paramedic or ambulance to pick up the patient and transfer to the emergency room. The system of the present disclosure also provides a prescription to uberized pharmacy with delivery to the patient. Additionally, the system collects feedback information either from the patient or a caretaker or uberized nurse that moved to the location of the patient to provide healthcare services to the patient. The method also decreases the probability of medical errors, guaranteeing continuity of care, re-evaluate if necessary and eliminate obstacles on a way of evaluation and management coding.

Figure 5:
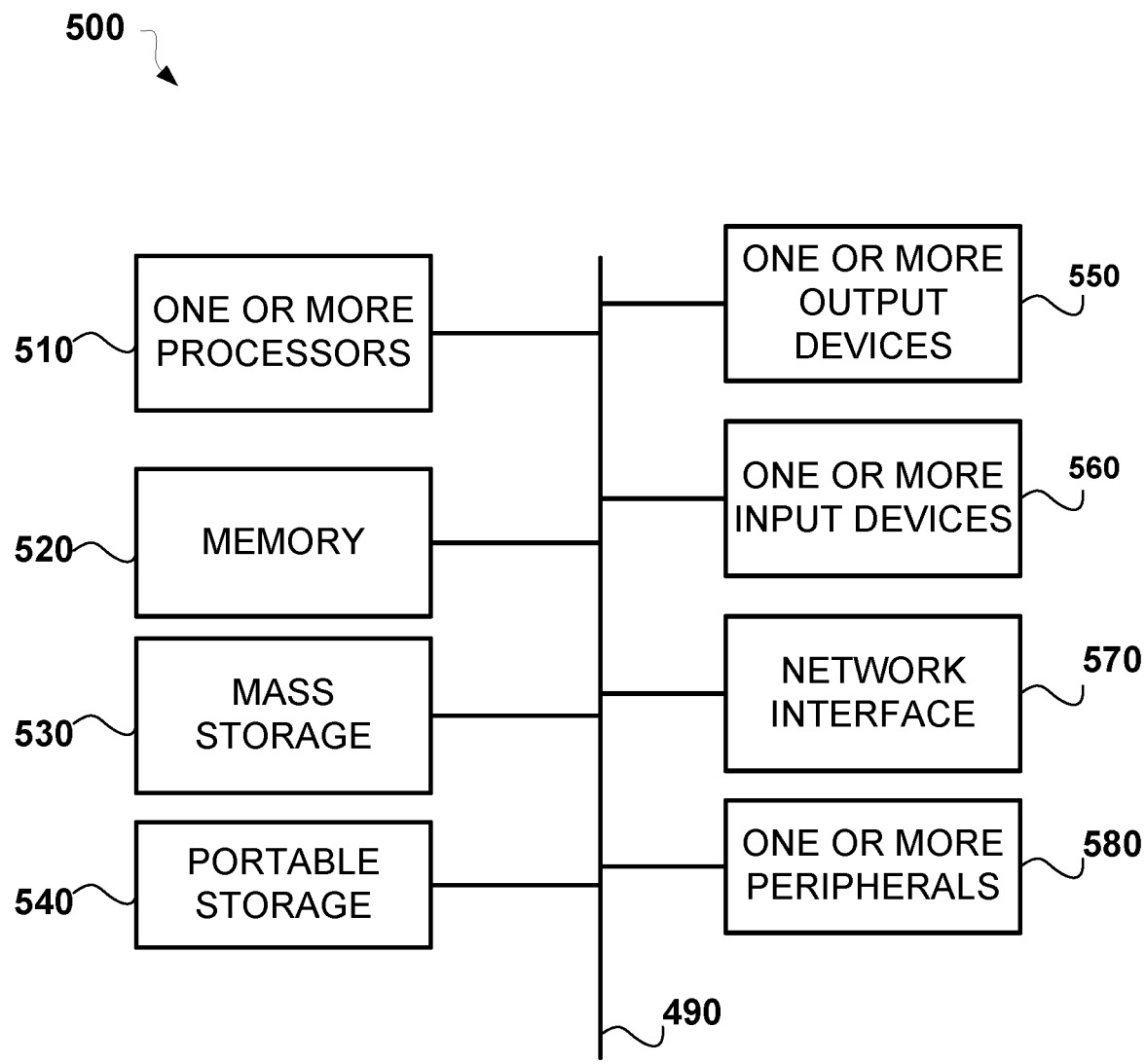
FIG. 5 is a block diagram illustrating an example computer system suitable for implementing systems and methods described herein.

FIG. 5 is a block diagram illustrating an example computer system 500 suitable for implementing the methods described herein. In particular, computer system 500 may be an instance of healthcare service center 105, diagnostic and laboratory service system 120, pharmacy service system 125, user device 130, or user device 135. FIG. 5 illustrates just one example of computer system 500 and in some embodiments computer system 500 may have fewer elements than shown in FIG. 5 or more elements than shown in FIG. 5.

Computer system 500 includes one or more processors 510, a memory 520, one or more storage devices 530, a portable storage 540, one or more input devices 550, one or more output devices 560, network interface 570, and one or more peripherals 580. These elements can be operatively interconnected via a communication bus 590. Processors 510 are, in some examples, configured to implement functionality and/or process instructions for execution within computer system 500. For example, processors 510 may process instructions stored in memory 520 and/or instructions stored on storage devices 530. Such instructions may include components of an operating system or software applications.

Memory 520, according to one example, is configured to store information within computer system 500 during operation. Memory 520, in some example embodiments, may refer to a non-transitory computer-readable storage medium or a computer-readable storage device. In some examples, memory 520 is a temporary memory, meaning that a primary purpose of memory 520 may not be long-term storage. Memory 520 may also refer to a volatile memory, meaning that memory 520 does not maintain stored contents when memory 520 is not receiving power. Examples of volatile memories include random access memories (RAM), dynamic random access memories (DRAM), static random access memories (SRAM), and other forms of volatile memories known in the art. In some examples, memory 520 is used to store program instructions for execution by the processors 510. Memory 520, in one example, is used by software. Generally, software refers to software applications suitable for implementing at least some operations of the methods as described herein.

Storage devices 530 can also include one or more transitory or non-transitory computer-readable storage media and/or computer-readable storage devices. In some embodiments, storage devices 530 may be configured to store greater amounts of information than memory 520. Storage devices 530 may further be configured for long-term storage of information. In some examples, the storage devices 530 include non-volatile storage elements. Examples of such non-volatile storage elements include magnetic hard discs, optical discs, solid-state discs, flash memories, forms of electrically programmable memories (EPROM) or electrically erasable and programmable memories, and other forms of non-volatile memories known in the art.

Still referencing to FIG. 5, computer system 500 may also include one or more input devices 550. Input devices 550 may be configured to receive input from a user through tactile, audio, video, or biometric channels. Examples of input devices 550 may include a keyboard, keypad, mouse, trackball, touchscreen, touchpad, microphone, one or more video cameras, image sensors, fingerprint sensors, or any other device capable of detecting an input from a user or other source and relaying the input to computer system 500 or components thereof.

Output devices 560, in some examples, may be configured to provide output to a user through visual or auditory channels. Output devices 560 may include a video graphics adapter card, a liquid crystal display (LCD) monitor, a light emitting diode (LED) monitor, an organic LED monitor, a sound card, a speaker, a lighting device, a LED, a projector, or any other device capable of generating output that may be intelligible to a user. Output devices 560 may also include a touchscreen, presence-sensitive display, or other input/output capable displays known in the art.

Computer system 500, in some example embodiments, also includes network interface 570. Network interface 570 can be utilized to communicate with external devices via one or more networks such as one or more wired, wireless, or optical networks including, for example, the Internet, intranet, local area network (LAN), wide area network (WAN), cellular phone networks (e.g. Global System for Mobile (GSM) communications network, packet switching communications network, circuit switching communications network), Bluetooth radio, and an IEEE 802.11-based radio frequency network, among others. Network interface 570 may be a network interface card, such as an Ethernet card, an optical transceiver, a radio frequency transceiver, or any other type of device that can send and receive information. Other examples of such network interfaces may include Bluetooth, 3G, 4G, LTE, and Wi-Fi radios in mobile computing devices.

Operating system of computer system 500 may control one or more functionalities of computer system 500 or components thereof. For example, the operating system of computer system 500 may interact with software applications of computer system 500 and may facilitate one or more interactions between the software applications and one or more of processors 510, memory 520, storage devices 530, input devices 550, and output devices 560. Operating system of computer system 500 may interact with the software applications and components thereof. In some embodiments, the software applications may be included in the operating system of computer system 500. In these and other examples, virtual modules, firmware, or software of the software applications. In other examples, virtual modules, firmware, or software may be implemented externally to computer system 500, such as at a network location. In some such instances, computer system 500 may use network interface 570 to access and implement functionalities provided by virtual modules, firmware, or software for vehicle identification through methods commonly known as "cloud computing."

Thus, methods and systems for providing healthcare services have been described. Although embodiments have been described with reference to specific example embodiments, it will be evident that various modifications and changes can be made to these example embodiments without departing from the broader spirit and scope of the present application. Accordingly, the specification and drawings are to be regarded in an illustrative rather than a restrictive sense.

What is claimed is:

1. A system for providing healthcare services, the system comprising:
   a healthcare service center including one or more computer servers and at least one database, the healthcare service center in communication with user devices of a plurality of patients and user devices of a plurality of healthcare providers;
   a first user interface configured to provide information to the plurality of patients and obtain inputs from the plurality of patients using a first graphical user interface, the first graphical user interface being displayable on the user devices of the plurality of patients; and
   a second user interface configured to provide information to the plurality of healthcare providers and obtain inputs from the plurality of healthcare providers using a second graphical user interface, the second graphical user interface being displayable on the user devices of the plurality of healthcare providers;
   wherein the healthcare service center is configured to:
      receive, from a requesting patient, a request for a healthcare service, the requesting patient being associated with patient preferences, the patient preferences being stored in a patient profile associated with the requesting patient, the patient profile being stored in the at least one database, wherein the at least one database further stores data associated with the plurality of healthcare providers;
      match the patient preferences and data obtained from the request with the data associated with the plurality of healthcare providers and to select, based on the matching, pre-selected healthcare providers from the plurality of healthcare providers;
      provide the request for the healthcare service to the pre-selected healthcare providers;
      receive, from a plurality of the pre-selected healthcare providers, a response to the request for the healthcare service, the response including an acceptance of the request for the healthcare service;
      upon the receipt of the response from the plurality of the pre-selected healthcare providers, provide a list of the plurality of the pre-selected healthcare providers to the requesting patient to enable the requesting patient to select a responding healthcare provider from the list of the plurality of the pre-selected healthcare providers that accepted the request for the healthcare service;
      establish a bidirectional communication between the requesting patient and the responding healthcare provider in real-time;

after establishing the bidirectional communication, receive, from the responding healthcare provider, a plan of actions to treat the requesting patient, the plan of actions being available to the requesting patient in an electronic medical record database;

receive, from the requesting patient, based on the plan of actions, a selection of a diagnostic and laboratory service, the diagnostic and laboratory service being associated with a location of the requesting patient and configured to collect real-time vital parameters of the requesting patient;

instruct the diagnostic and laboratory service to physically contact the requesting patient at the location of the requesting patient and collect the real-time vital parameters, the diagnostic and laboratory service including a self-driving vehicle, the self-driving vehicle having a diagnostic equipment, the diagnostic equipment being configured to collect body fluids and the real-time vital parameters of the requesting patient, the self-driving vehicle being configured to drive, based on the instruction, to the location of the requesting patient and collect at least the real-time vital parameters at the location of the requesting patient using the diagnostic equipment associated with the self-driving vehicle;

receive, from the diagnostic and laboratory service, the real-time vital parameters of the requesting patient and make the real-time vital parameters available to the requesting patient and the responding healthcare provider in the electronic medical record database;

analyze at least the real-time vital parameters and the patient profile;

based on the analysis, determine a preliminary diagnosis of the requesting patient; and send the preliminary diagnosis to at least the responding healthcare provider.

2. The system of claim 1, wherein the receiving of the plan of actions includes receiving of one of an emergency plan of actions and a non-emergency plan of actions, wherein:
the receiving of the emergency plan of actions includes receiving an instruction to forward an emergency medical service to the requesting patient; and
the receiving of the non-emergency plan of actions includes receiving a digital diagnostic request to collect the real-time vital parameters of the requesting patient.

3. The system of claim 1, wherein the healthcare service center is further configured to, based on the location of the requesting patient and the plan of actions received from the responding healthcare provider, instruct the responding healthcare provider to move to the location of the requesting patient to provide treatment according to the plan of actions.

4. The system of claim 1, wherein the healthcare service center is further configured to:
upon terminating the bidirectional communication, receive a further request from the requesting patient to contact the responding healthcare provider; and
in response to the request, re-establish the bidirectional communication between the requesting patient and the responding healthcare provider.

5. The system of claim 1, wherein the healthcare service center is further configured to:
upon terminating the bidirectional communication, receive a further request from the responding healthcare provider to contact the requesting patient; and
in response to the request, re-establish the bidirectional communication between the responding healthcare provider and the requesting patient.

6. The system of claim 1, wherein the healthcare service center is further configured to:
receive a digital prescription from the responding healthcare provider, the digital prescription being associated with the requesting patient; and
select and cause one of a plurality pharmacy service systems to deliver a medication to the requesting patient in accordance with the digital prescription, the one of a plurality pharmacy service systems being associated with the location of the requesting patient.

7. The system of claim 1, wherein the healthcare service center is further configured to:
receive, from the requesting patient, patient data, the patient data including at least medical data and the location of the requesting patient; and
store the patient data to the electronic medical record database.

8. The system of claim 1, wherein the healthcare service center is further configured to:
make the real-time vital parameters of the requesting patient available to a plurality of healthcare providers via the electronic medical record database;
receive, from one or more of the plurality of healthcare providers, one or more requests to provide healthcare services to the requesting patient;
report to the requesting patient the one or more requests from the one or more of the plurality of healthcare providers;
receive, from the requesting patient, a selection of one of the one or more of the plurality of healthcare providers; and
based on the selection, establish a further bi-directional communication between the requesting patient and the one of the one or more of the plurality of healthcare providers.

9. A method for providing healthcare services, the method comprising:
receiving, by one or more computer servers associated with a healthcare service center, from a requesting patient, a request for a healthcare service, the requesting patient being associated with patient preferences, the patient preferences being stored in a patient profile associated with the requesting patient, the patient profile being stored in at least one database associated with the healthcare service center, wherein the at least one database further stores data associated with a plurality of healthcare providers;
matching, by the one or more computer servers, the patient preferences and data obtained from the request with the data associated with the plurality of healthcare providers to select, based on the matching, pre-selected healthcare providers from the plurality of healthcare providers;
providing the request for healthcare service to the pre-selected healthcare providers;
receiving, from a plurality of the pre-selected healthcare providers, a response to the request for the healthcare service, the response including an acceptance of the request for the healthcare service;
upon the receiving the response from the plurality of the pre-selected healthcare providers, providing a list of the plurality of the pre-selected healthcare providers to the requesting patient to enable the requesting patient to select a responding healthcare provider from the list of the plurality of the pre-selected healthcare providers that accepted the request for the healthcare service;

establishing a bidirectional communication between the requesting patient and the responding healthcare provider in real-time;

upon the establishing the bidirectional communication, receiving, from the responding healthcare provider, a plan of actions to treat the requesting patient, the plan of actions being available to the requesting patient in an electronic medical record database;

receiving, from the requesting patient, based on the plan of actions, a selection of a diagnostic and laboratory service, the diagnostic and laboratory service being associated with a location of the requesting patient and configured to collect real-time vital parameters of the requesting patient;

instructing the diagnostic and laboratory service to physically contact the requesting patient at the location of the requesting patient and collect the real-time vital parameters, the diagnostic and laboratory service including a self-driving vehicle, the self-driving vehicle having a diagnostic equipment, the diagnostic equipment being configured to collect body fluids and the real-time vital parameters of the requesting patient, the self-driving vehicle being configured to drive, based on the instruction, to the location of the requesting patient and collect at least the real-time vital parameters at the location of the requesting patient using the diagnostic equipment associated with the self-driving vehicle;

receiving, from the diagnostic and laboratory service, the real-time vital parameters of the requesting patient and making the real-time vital parameters available to the requesting patient and the responding healthcare provider in the electronic medical record database;

analyzing, by the one or more computer servers, at least the real-time vital parameters and the patient profile;

based on the analysis, determining, by the one or more computer servers, a preliminary diagnosis of the requesting patient; and sending, by the one or more computer servers, the preliminary diagnosis to at least the responding healthcare provider.

10. The method of claim 9, wherein the receiving of the plan of actions includes receiving of one of an emergency plan of actions and a non-emergency plan of actions, wherein:

the receiving of the emergency plan of actions includes receiving an instruction to forward an emergency medical service to the requesting patient; and the receiving of the non-emergency plan of actions includes receiving a digital diagnostic request to collect the real-time vital parameters of the requesting patient.

11. The method of claim 9, further comprising, based on the location of the requesting patient and the plan of actions received from the responding healthcare provider, instructing the responding healthcare provider to move to the location of the requesting patient to provide treatment according to the plan of actions.

12. The method of claim 9, further comprising:

upon terminating the bidirectional communication, receiving a further request from the requesting patient to contact the responding healthcare provider; and in response to the request, re-establishing the bidirectional communication between the requesting patient and the responding healthcare provider.

13. The method of claim 9, further comprising:

upon terminating the bidirectional communication, receiving a further request from the responding healthcare provider to contact the requesting patient; and in response to the request, re-establishing the bidirectional communication between the responding healthcare provider and the requesting patient.

14. The method of claim 9, further comprising:

receiving a digital prescription from the responding healthcare provider, the digital prescription being associated with the requesting patient; and selecting and causing one of a plurality pharmacy service systems to deliver a medication to the requesting patient in accordance with the digital prescription, the one of a plurality pharmacy service systems being associated with the location of the requesting patient.

15. The method of claim 9, further comprising:

receiving, from the requesting patient, patient data, the patient data including at least medical data and the location of the requesting patient; and storing the patient data to the electronic medical record database.

16. The method of claim 15, further comprising prompting the requesting patient to enter the medical data, the medical data being associated with one or more of the following: a current health condition, previous treatment episodes, vaccinations, routine tests, and hospitalizations.

17. The method of claim 9, further comprising:

making the real-time vital parameters of the requesting patient available to a plurality of healthcare providers via the electronic medical record database;

receiving, from one or more of the plurality of healthcare providers, one or more requests to provide healthcare services to the requesting patient;

reporting to the requesting patient the one or more requests from the one or more of the plurality of healthcare providers;

receiving, from the requesting patient, a selection of one of the one or more of the plurality of healthcare providers; and based on the selection, establishing a further bi-directional communication between the requesting patient and the one of the one or more of the plurality of healthcare providers.

18. A system for providing healthcare services, the system comprising:

a healthcare service center including one or more computer servers and at least one database, the healthcare service center being in communication with user devices of a plurality of patients and user devices of a plurality of healthcare providers;

a first user interface configured to provide information to the plurality of patients and obtain inputs from the plurality of patients using a first graphical user interface, the first graphical user interface being displayable on the user devices of the plurality of patients;

a second user interface configured to provide information to the plurality of healthcare providers and obtain inputs from the plurality of healthcare providers using a second graphical user interface, the second graphical user interface being displayable on the user devices of the plurality of healthcare providers;

wherein the healthcare service center is configured to:

receive, from a requesting patient, a request for a healthcare service, the requesting patient being associated with patient preferences, the patient preferences being stored in a patient profile associated with the requesting patient, the patient profile being stored in the at least one database, wherein the at least one database further stores data associated with the plurality of healthcare providers;

match the patient preferences and data obtained from the request with the data associated with the plurality of healthcare providers to select, based on the matching, pre-selected healthcare providers from the plurality of healthcare providers;

provide the request for the healthcare service to the pre-selected healthcare providers;

receive, from a plurality of the pre-selected healthcare providers, a response to the request for the healthcare service, the response including an acceptance of the request for the healthcare service;

upon the receipt of the response from the plurality of the pre-selected healthcare providers, provide a list of the plurality of the pre-selected healthcare providers to the requesting patient to enable the requesting patient to select a responding healthcare provider from the list of the plurality of the pre-selected healthcare providers that accepted the request for the healthcare service;

establish a bidirectional communication between the requesting patient and the responding healthcare provider in real-time;

after establishing the bidirectional communication, receive, from the responding healthcare provider, a plan of actions to treat the requesting patient, the plan of actions being available to the requesting patient in an electronic medical record database;

receive, from the requesting patient, based on the plan of actions, a selection of a diagnostic and laboratory service, the diagnostic and laboratory service being associated with a location of the requesting patient and configured to collect real-time vital parameters of the requesting patient;

instruct the diagnostic and laboratory service to physically contact the requesting patient at the location of the requesting patient and collect the real-time vital parameters, the diagnostic and laboratory service including a self-driving vehicle, the self-driving vehicle having a diagnostic equipment, the diagnostic equipment being configured to collect body fluids and the real-time vital parameters of the requesting patient, the self-driving vehicle being configured to drive, based on the instruction, to the location of the requesting patient and collect at least the real-time vital parameters at the location of the requesting patient using the diagnostic equipment associated with the self-driving vehicle;

receive, from the diagnostic and laboratory service, the real-time vital parameters of the requesting patient and make the real-time vital parameters available to the requesting patient and the responding healthcare provider in the electronic medical record database;

make the real-time vital parameters of the requesting patient available to a plurality of healthcare providers via the electronic medical record database;

receive, from one or more of the plurality of healthcare providers, one or more requests to provide healthcare services to the requesting patient;

report to the requesting patient the one or more requests from the one or more of the plurality of healthcare providers;

receive, from the requesting patient, a selection of one of the one or more of the plurality of healthcare providers;

based on the selection, establish a further bi-directional communication between the requesting patient and the one of the one or more of the plurality of healthcare providers;

analyze at least the real-time vital parameters and the patient profile;

based on the analysis, determine a preliminary diagnosis of the requesting patient; and send the preliminary diagnosis to at least the responding healthcare provider.

\* \* \* \* \*